(12) United States Patent
Aleksandrovic-Bondzic et al.

(10) Patent No.: US 10,023,668 B2
(45) Date of Patent: Jul. 17, 2018

(54) THICKENED POLYMER

(75) Inventors: Vesna Aleksandrovic-Bondzic, Hamburg (DE); Sascha Mertens, Reinbek (DE); Stephan Foerster, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 1237 days.

(21) Appl. No.: 13/700,406

(22) PCT Filed: Mar. 21, 2011

(86) PCT No.: PCT/EP2011/054247
§ 371 (c)(1),
(2), (4) Date: Apr. 19, 2013

(87) PCT Pub. No.: WO2011/151091
PCT Pub. Date: Dec. 8, 2011

(65) Prior Publication Data
US 2013/0203866 A1 Aug. 8, 2013

(30) Foreign Application Priority Data

May 31, 2010 (DE) .................. 10 2010 022 063

(51) Int. Cl.
| | |
|---|---|
| *C08F 220/06* | (2006.01) |
| *C08F 220/18* | (2006.01) |
| *C08F 220/26* | (2006.01) |
| *C08F 120/68* | (2006.01) |
| *A61K 8/81* | (2006.01) |
| *C08F 2/22* | (2006.01) |
| *C08F 220/04* | (2006.01) |
| *A61Q 19/00* | (2006.01) |
| *C08F 128/02* | (2006.01) |
| *C08F 222/10* | (2006.01) |
| *C08F 216/14* | (2006.01) |

(52) U.S. Cl.
CPC .......... *C08F 120/68* (2013.01); *A61K 8/8152* (2013.01); *A61Q 19/00* (2013.01); *C08F 2/22* (2013.01); *C08F 128/02* (2013.01); *C08F 220/04* (2013.01); *C08F 220/18* (2013.01); *A61K 2800/10* (2013.01); *A61K 2800/48* (2013.01); *C08F 220/06* (2013.01); *C08F 222/1006* (2013.01); *C08F 2216/145* (2013.01); *C08F 2220/1891* (2013.01)

(58) Field of Classification Search
CPC .... C08F 120/68; C08F 220/04; C08F 220/18; C08F 220/06; C08F 2220/1891; C08F 222/1006
See application file for complete search history.

(56) References Cited

U.S. PATENT DOCUMENTS

| | | | |
|---|---|---|---|
| 4,110,291 A * | 8/1978 | Barabas et al. ............... | 524/501 |
| 6,242,531 B1 | 6/2001 | Craun et al. | |
| 6,906,151 B2 | 6/2005 | Throne et al. | |
| 7,081,507 B2 | 7/2006 | Morschhaeuser et al. | |
| 7,153,496 B2 | 12/2006 | Tamareslvy et al. | |
| 7,288,616 B2 | 10/2007 | Tamareslvy et al. | |
| 7,649,042 B2 | 2/2010 | Tamareselvy et al. | |
| 7,947,771 B2 | 5/2011 | Riegel et al. | |
| 2003/0202953 A1 * | 10/2003 | Tamareselvy et al. .... | 424/70.16 |
| 2003/0207988 A1 | 11/2003 | Tamareselvy et al. | |
| 2004/0087668 A1 | 5/2004 | Schmucker-Castner et al. | |
| 2004/0143074 A1 | 7/2004 | Throne et al. | |
| 2005/0032998 A1 | 2/2005 | Morschhaeuser et al. | |
| 2006/0251600 A1 | 11/2006 | Tamareselvy et al. | |
| 2007/0161524 A1 | 7/2007 | Counradi et al. | |
| 2007/0293617 A1 | 12/2007 | Riegel et al. | |
| 2008/0045646 A1 | 2/2008 | Tamareselvy et al. | |

FOREIGN PATENT DOCUMENTS

| | | |
|---|---|---|
| EP | 1465932 A1 | 10/2004 |
| WO | 0176552 A2 | 10/2001 |
| WO | 03061615 A1 | 7/2003 |
| WO | 03062288 A1 | 7/2003 |
| WO | 2005030163 A1 | 4/2005 |
| WO | 2007090759 A1 | 8/2007 |

* cited by examiner

Primary Examiner — Karuna P Reddy
(74) Attorney, Agent, or Firm — Abel Law Group, LLP

(57) ABSTRACT

The invention relates to a polymer which can be obtained by radical emulsion polymerization of at least one acidic vinyl monomer or salt thereof, at least one non-ionic vinyl monomer, in particular preferably a hydrophobic non-ionic vinyl monomer, at least one monomer containing an unsaturated terminal group and a polyoxyalkyene portion, at least one crosslinking monomer, optionally a protective colloid, and is characterized in that the polymerization is controlled such that the gelling effect occurs at least at times, which is achieved by the monomer addition (dosing time) taking place for 40 minutes, particularly preferably for 30 minutes.

18 Claims, No Drawings

THICKENED POLYMER

BACKGROUND OF THE INVENTION

1. Field of the Invention

The invention relates to a new type of thickening polymer with special properties which is free from associative monomers and/or whose chain contains no such associative monomers.

Definitions

Unless stated otherwise, all quantitative data are percentages by mass based on the total mass of the preparation.

Within the context of the present specification, associative monomers are monomers of the type U-S-L, where U contains an ethylenically unsaturated group such as methacrylate, acrylate, allyl or vinyl groups, S is a spacer from a polyoxyalkylene chain having 2 to 300 alkyleneoxy units such as polyethylene glycol, polypropylene glycol or polybutylene glycol, and L is a hydrophobic group such as an alkyl and/or aryl group, which has at least 4, preferably at least 8 carbon atoms, for example a lauryl group.

Within the context of the present specification, tan δ value means the quotient of the loss modulus and the storage modulus, in each case measured at 40° C. The measuring device used here is not important. The values given in this specification were determined using the Malvern Gemini HR nano.

2. Discussion of Background Information

In general, thickening polymers serve to thicken water or water-containing preparations. In this connection, the water allows the polymers to swell to gels in order, in so doing, to influence viscosity and flow behavior. Thickening polymers are of importance in the manufacture of body cleansing compositions, creams, cleaning compositions, finishes, printing inks, coatings, emulsion paints and other coating materials, adhesives, paper, foods and so on.

Known from EP 1465932 B1 were alkali-swellable and alkali-soluble associative multipurpose polymers which is the polymerization product of a monomer mixture of
a) at least one acid-containing vinyl monomer,
b) at least one nonionic vinyl monomer,
c) a first associative monomer which has a first hydrophobic end group,
d) a second associative monomer with a second hydrophobic end group, a semi-hydrophobic monomer and of a combination thereof and optionally
e) one or more crosslinking monomers or chain-transfer agents.

Such polymers are prepared by emulsion polymerization. For this, firstly the monomer mixture is emulsified or suspended with a surfactant in water in the form of micelles. The actual reactor is charged with the initiator in aqueous solution or suspension, and the monomer suspension is slowly added. The rate at which the monomer is added is controlled so as to avoid a considerable increase in the reaction temperature as a result of the Trommsdorff effect (gel effect). The gel effect arises in the event of too great an increase in the conversion and leads to the rate of the polymerization increasing as a result of diffusion of the polymer radicals being hindered, and the polymerization in itself is accelerated. Attempts are made to prevent this for reasons of safety and to obtain a narrow molar mass distribution. If the gel effect does arise, then a bimodal molar mass distribution is obtained. Further prior art can be found in EP 1272159, WO03062288, WO03061615, WO03062288, WO2007090759, U.S. Pat. No. 6,242,531.

Thickening polymers with which it is possible to thicken aqueous preparations such that gels which are as clear as possible are formed are desirable.

Thickening polymers with which tan δ values which are as low as possible can be achieved in aqueous solution are also desirable.

Thickening polymers with a considerably extended storage stability are likewise desirable.

The prior art lacked thickening polymers which make it possible to produce clear gels coupled with simultaneously low tan δ values.

SUMMARY OF THE INVENTION

Surprisingly and unforeseeably to the person skilled in the art, it has now been found that a polymer obtainable by free-radical emulsion polymerization of
(A) at least one acidic vinyl monomer or salt thereof,
(B) at least one nonionic vinyl monomer, particularly preferably a hydrophobic nonionic vinyl monomer,
(C) at least one monomer containing an unsaturated end group and a polyoxyalkylene portion,
(D) at least one crosslinking monomer,
(E) optionally a protective colloid, characterized in that the polymerization is controlled such that at least at times the gel effect arises, achieved by the fact that the monomer addition (dosing time) takes place over the course of 40 minutes, particularly preferably over the course of 30 minutes, overcomes the defects of the prior art. In the case of such a polymerization utilizing the Trommsdorff effect, i.e. with the constant addition of the monomers and simultaneously high addition rate of the monomers, a monomer excess is formed which leads to an autoacceleration of the polymerization (Trommsdorff effect). The result is an increase in the molecular weights coupled with simultaneously advantageous morphology of the polymers. In this connection, it is particularly preferred if (F) associative monomers are not present or have at most a concentration of 15% by weight, preferably 10% by weight, particularly preferably 5% by weight, very particularly preferably 2.5% by weight, very extraordinarily preferably 1% by weight, very particularly extraordinarily preferably 0.1% by weight. It is particularly preferred if the acidic vinyl monomer (A) is selected from vinyl monomers with carboxyl groups, particularly preferably acrylic acid or methacrylic acid or alkali metal, alkaline earth metal, ammonium or alkylammonium salts thereof, very particularly preferably methacrylic acid or alkali metal, alkaline earth metal, ammonium or alkylammonium salts thereof. It is particularly preferred if the nonionic vinyl monomer (B) is selected from C1-C22-alkyl (meth)acrylates and mixtures thereof. As a result, good flow properties and thus an advantageous rheological profile are achieved.

Additional long-chain alkyl acrylates (C12 and C18) are particularly preferred because they increase the viscosity that can be achieved. It is particularly preferred if the monomer (C) containing an unsaturated end group and a polyoxyalkylene portion is selected from vinylpolyalkylene glycols or polymerizable surfactants or mixtures thereof, is particularly preferably selected from R307, RAL307, A11/1800, R1100, AMR, AB25-8. It is particularly preferred if the crosslinking monomer (D) is selected from polyol (meth)acrylates with at least two (meth)acrylate groups and the mixed esters of polyols with acrylic acid and/or methacrylic acid. It is further particularly preferred if the monomers (A) are present in contents of from 10 to 75%, preferably 30 to 50%, particularly preferably 35 to 49%, (B) are present in contents of from 10 to 90%, preferably 30 to 80%, particularly preferably 47 to 60%, (C) are present in contents of from 0.5 to 40%, preferably 1 to 10%, particularly preferably 2 to 6%, (D) are present in contents of up to 1%, preferably 0.05 to 0.5%, particularly preferably 0.1 to 0.35%. It is very particularly preferred if the monomers (A):(B) are present in mass ratios of from 1:2 to 2:1. It is very particularly preferred if the polymer is selected from example 22, 24, 25, 28, 35, 37, 40 or 52. The invention also encompasses a thickened preparation comprising a polymer as claimed in any one of the preceding claims. It is particularly preferred if the use concentration of the polymer for thickening aqueous, preferably surfactant-containing aqueous, preparations is 2 to 3%. As a result, the preparation becomes transparent at pH values <6.5 and has a viscosity of at least 3000 mPa·s, which means that added suspended substances do not settle out, possible suspended substances being beads, pigments or air bubbles. It is particularly preferred if the preparations according to the invention are a health product, cleaning product, household product, shower gel, paint, inks, dispersant, antisettling agent, concrete and cement additive, coatings, medicinal product, cosmetic product or dermatological product. The invention also encompasses the use of a polymer according to the invention as thickener, emulsifier, dispersant or consistency regulator.

DETAILED DESCRIPTION OF THE INVENTION

The preparations—if they are gel-like preparations with yield point—are advantageously designed such that they have a yield point of 0.5-20 Pa, preferably 1-6 Pa.

The yield point is considered to be the critical shear stress of the flow curve. It can be ascertained according to the invention as follows:

The flow curve is measured on a shear-stress-controlled rheometer at 25° C.±1° C. with 20 mm plate/plate geometry with a gap between 0.8 mm and 1.2 mm, with charging being carried out in a structure-preserving manner. A suitable constant shear stress gradient is pregiven and, before the test, a corresponding structure recovery time is observed and the critical shear stress at the maximum of the flow curve is given.

Advantageously, the preparations are designed such that they have a tan δ of 0.05-0.6, preferably 0.1-0.5.

According to the invention, tan δ is understood as meaning the quotient of the loss modulus and the storage modulus. The tan δ is ascertained as follows:

Loss and storage moduli are measured by a dynamic frequency test on a shear-stress-controlled rheometer at 40° C.±1° C. with 20 mm plate/plate geometry with a gap between 0.8 mm and 1.2 mm, charging being carried out in a structure-preserving manner. The frequency test is carried out according to the prior art with an appropriate structure recovery time before the test, and the tan δ in the frequency range between 0.05 rad/s and 3.0 rad/s is quoted, preferably between 0.08 rad/s and 1.0 rad/s.

The preparations are advantageously designed such that, at pH<6.2, they have a turbidity value of NTU (Nephelometric Turbidity Unit)<20. The turbidity value is measured using a turbidity measuring device, with distilled water having a value of NTU=0 serving as standard.

It is also in accordance with the invention if not water, but other polar liquids are thickened by polymers according to the invention. In particular, alcohols, glycols, polyols, amines and organic acids such as for example acrylic acid can be thickened.

The use of polymers according to the invention as emulsifier is also in accordance with the invention. In this way, creams and lotions can be provided.

The polymers are also suitable as dispersants and antisettling agents.

EXAMPLES

Synthesis of the Copolymers

The examples below aim to illustrate the present invention without limiting it. The preparation of the examples takes place in accordance with the method described below, the type and amounts of the monomers, chain-transfer agents and protective colloids each used as starting components being summarized in Table 2. Parts and percentages refer to the weight.

Example 1

| Monomer phase | |
| --- | --- |
| Methacrylic acid | 37.000 parts |
| Ethyl acrylate | 51.800 parts |
| Octadecyl acrylate | 5.000 parts |
| Emulsogen R307 | 6.000 parts |
| Trimethylolpropane triacrylate | 0.300 parts |
| Water phase | |
| Water | 33.060 parts |
| Sodium lauryl sulfate | 0.984 parts |
| Reaction vessel | |
| Water | 173.146 parts |
| Sodium lauryl sulfate | 0.300 parts |
| Initiator phase A | |
| Water | 1.911 parts |
| Ammonium persulfate | 0.069 parts |
| Initiator phase B | |
| Water | 2.909 parts |
| Ammonium persulfate | 0.021 parts |

The reaction vessel, which is equipped with stirrer, reflux condenser, nitrogen feed, dosing device and internal thermometer, is charged with 173.146 parts of water and 0.300 parts of sodium lauryl sulfate. The mixture is heated to 82° C. with stifling and under a nitrogen atmosphere.

The monomer mixture is prepared in a second stirred vessel which is equipped with stirrer and nitrogen feed. For this purpose, the monomer phase with 37.000 parts methacrylic acid, 51.800 parts ethyl acrylate, 5.000 parts octadecyl acrylate, 6.000 parts Emulsogen R307 and 0.300 parts trimethylpropane triacrylate is introduced, and into this is mixed the water phase with 33.060 parts water and 0.984 parts sodium lauryl sulfate with stirring and under a nitrogen atmosphere.

As soon as a temperature of 82° C. is reached in the reaction vessel, an initiator phase A, consisting of 0.069 parts ammonium persulfate and 1.911 parts of water, is added and the monomer mixture is metered in uniformly at 85-88° C. over the course of 30 minutes. Then, an initiator phase B, consisting of 0.021 parts ammonium persulfate and 2.909 parts water, is added and then the reaction mixture is post-polymerized for a further 4 hours at 90° C. before being cooled to <40° C.

Examples 2-52

The examples below (Table 1) are prepared analogously to Example 1. In most examples, sodium lauryl sulfate was used as emulsifier. In a departure from this, Examples 5 and 11 were prepared from a combination of sodium lauryl sulfate and ethoxylated isotridecyl alcohol (Genapol X1005, Clariant), and Example 10 was prepared with isotridecyl alcohol (Genapol X1005, Clariant).

Abbreviations

MAA Methacrylic acid
EA Ethyl acrylate
LA Lauryl acrylate
ODA Octadecyl acrylate
S20W Bisomer® S20W (Cognis)
  Methoxypolyethylene glycol methacrylate (EO 45 mol)
M5010 Maxemul® 5010 (Croda)
  $C_{12}H_{23}HCCH(C_2H_4O_{25}CH_3$
R307 Emulsogen® R307 (Clariant)
  EO/PO 30 1,4-butanediol vinyl ether (EO/PO 30 mol)
RAL307 Emulsogen® RAL307 (Clariant)
  Allylpolyalkylene glycol ether (EO 30 mol)
R208 Emulsogen® R208 (Clariant)
  1,4-Butanediol vinyl ether (EO/PO 25 mol)
A11/1800 Polyglycol A11/1800 (Clariant)
  Allylpolyalkylene glycol ether (EO 20 mol, PO 20 mol)
R500 Polyglycol R500 (Clariant)
  Vinylpolyalkylene glycol ether (EO 9 mol)
R1100 Polyglycol R1100 (Clariant)
  Vinylpolyalkylene glycol ether (EO 20 mol)
R2000 Polyglycol R2000 (Clariant)
  Vinylpolyalkylene glycol ether (EO 40 mol)
AM 20/20 Polyglycol AM 20/20 (Clariant)
  Polyalkylene glycol allyl methyl ether (EO 20 mol, PO 20 mol)
AB 1500 Polyglycol AB1500 (Clariant)
  Polypropylene glycol allyl butyl ether (PO 25 mol)
AB/25-8 Polyglycol AB/25-8 (Clariant)
  Polyalkylene glycol allyl butyl ether (EO 25 mol, PO 8 mol)
A31/1600 Polyglycol A31/1600 (Clariant)
  Polyalkylene glycol allyl ether (EO 25 mol, PO 8 mol)
A 10 R Pluriol® A10R (BASF)
  Allyl alcohol alkoxylates
A 111 R Pluriol® A111R (BASF)
  Allyl alcohol alkoxylates
SPE RALU®MER SPE (Raschig)
  Dimethyl[2-[(2-methyl-1-oxoallyl)oxy]ethyl](3-sulfopropyl)ammonium hydroxide
SPM RALU®MER SPM (Raschig)
  Potassium 3-sulfopropylmethacrylate
SPP RALU®MER SPP (Raschig)
  Dimethyl[3-[(2-methyl-1-oxoallyl)amino]propyl]-3-sulfopropylammonium hydroxide
HMP Bisomer® HMP (Cognis)
  Monoester of maleic acid and C16-18 fatty alcohol
KH-10 Hitenol® KH-10 (Dai-Ichi Kogyo Seiyaku)
  Ammonium polyoxyalkylene-1-(allyloxymethyl)alkyl ether sulfate

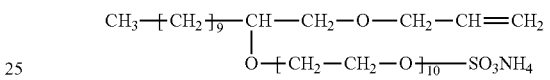

BC-10 Hitenol® BC-10 (Dai-Ichi Kogyo Seiyaku)
  Ammonium nonylphenol polyoxyethylene alkyl ether sulfate

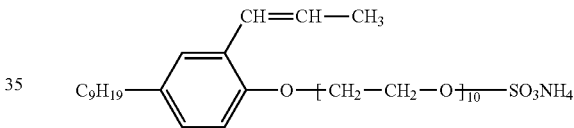

BEM Behenyl ethylene glycol-1100 methacrylate
TMPTA Trimethylolpropane triacrylate
TMPTMA Trimethylolpropane trimethacrylate
IMP Isooctyl 3-mercaptopropionate
AMHEC Tylose AM H40 YP2 (SE Tylose)
  Allyl-modified hydroxyethylcellulose

TABLE 1

Examples 1-52

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| MAA | 37 | 37 | 37 | 37 | 37 | 37 | 37 | 37 | 37 | 37 | 37 | 37 | 37 | 37 | 37 | 37 | 37 | 37 | 37 | 37 | 37 | 37 | 37 | 37 | 37 | 37 | 37 |
| EA | 51.5 | 53.5 | 53.5 | 53.5 | 51.5 | 53.5 | 53.5 | 53.5 | 53.5 | 53.5 | 53.5 | 47.5 | 53.5 | 53.5 | 53.5 | 53.5 | 51.5 | 51.5 | 51.6 | 53.5 | 53.5 | 53.5 | 53.5 | 52.5 | 54.5 | 33.5 | 56.5 |
| ODA | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
| LA | | | | 2 | 2 | | | | | | | | | | | | | | | | | | | | | | |
| S20W | | 2 | | | | | | 2 | 2 | 2 | 2 | | | | | | | | | | | | | | | | |
| M5010 | 6 | 2 | 2 | | 2 | 2 | | 2 | | 2 | 2 | | | | | | | | | | | | | 2 | | | |
| R307 | | | | | | | 4 | | | | | | | | | | | | | | | | | | | | |
| RAL307 | | | | 2 | | | | | | | | | | | | | | | | | | | | | | | |
| R208 | | | 2 | | 2 | 2 | | 2 | 2 | 2 | 2 | 10 | 2 | 2 | 2 | 2 | 6 | 6 | 6 | 2 | 2 | | 2 | | | | |
| A11/18 | | | | | | | | | | | | | | | | | | | | | | 6 | | 5.4 | | | |
| R500 | | | | | | | | | | | | | | | | | | | | | | | | | | 24 | |
| R1100 | | | | | | | | | | | | | | | | | | | | | | | | | 2.9 | | |
| R2000 | | | | | | | | | | | | | | | | | | | | | | | | | | | |
| AM | | | | | | | | | | | | | | | | | | | | | | | | | | | |
| AB | | | | | | | | | | | | | | | | | | | | | | | | | | | |
| AB/25-8 | | | | | | | | | | | | | | | | | | | | | | | | | | | |
| A31/16 | | | | | | | | | | | | | | | | | | | | | | | | | | | |
| A 10 R | | | | | | | | | | | | | | | | | | | | | | | | | | | 1.7 |
| A 111 R | | | | | | | | | | | | | | | | | | | | | | | | | | | |
| SPE | | | | | | | | | | | | | 2 | | | | | | | | | | | | | | |
| SPM | | | | | | | | | | | | | | 2 | | | | | | | | | | | | | |
| SPP | | | | | | | | | | | | | | | 2 | | | | | | | | | | | | |
| HMP | | | | | | | | | | | | | | | | 2 | | | | | | | | | | | |
| KH-10 | | | | | | | | | | | | | | | | | 0.3 | | | 2 | | | | | | | |
| BC-10 | | | | | | | | | | | | | | | | | | 0.3 | 0.3 | | 2 | | | | | | |
| BEM | | | | | | | | | | | | | | | | | | | | | | | | | | | |
| TMPTA | 0.3 | 0.3 | 0.3 | 0.3 | 0.3 | 0.3 | 0.3 | 0.5 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 |
| TMPTM | | | | | | | | | | | | | | | | | | | | | | | | | | | |
| IMP | | | | | | | | | | | | | | | | | | 0.0 | 0.15 | | | | | | | | |
| AMHEC | | | | | | | | | | | | | | | | | | | | | | | | | | | |

TABLE 2

Results for polymer emulsions

| Example | pH value | Particle size* in nm |
|---|---|---|
| 1 | 2.48 | 108 |
| 2 | 2.47 | 103 |
| 3 | n.d. | n.d. |
| 4 | n.d. | n.d. |
| 5 | n.d. | n.d. |
| 6 | n.d. | n.d. |
| 7 | n.d. | n.d. |
| 8 | n.d. | n.d. |
| 9 | n.d. | n.d. |
| 10 | n.d. | n.d. |
| 11 | n.d. | n.d. |
| 12 | n.d. | n.d. |
| 14 | 2.57 | 102 |
| 14 | 2.62 | 129 |
| 15 | 3.13 | 95 |
| 16 | 2.14 | 186 |
| 17 | 2.53 | 88 |
| 18 | 2.52 | 107 |
| 19 | 2.51 | 101 |
| 20 | 2.53 | 79 |
| 21 | 2.54 | 79 |
| 22 | 2.50 | 96 |
| 23 | 2.52 | 89 |
| 24 | 2.55 | 87 |
| 25 | 2.47 | 111 |
| 26 | 2.67 | 165 |
| 27 | 2.76 | 89 |
| 28 | 2.50 | 87 |
| 29 | 2.56 | 103 |
| 30 | 2.58 | 87 |
| 31 | 2.57 | 95 |
| 32 | 2.48 | 79 |
| 33 | 2.30 | 104 |
| 34 | 2.37 | 96 |
| 35 | 2.46 | 85 |
| 36 | 2.36 | 85 |
| 37 | 2.46 | 113 |
| 38 | 2.39 | 89 |
| 39 | 2.37 | 96 |
| 40 | 2.38 | 94 |
| 41 | 2.65 | 85 |
| 42 | 2.32 | 103 |
| 43 | 2.42 | 91 |
| 44 | 2.39 | 90 |
| 45 | 2.36 | 87 |
| 46 | 2.42 | 101 |
| 47 | 2.34 | 84 |
| 48 | 2.40 | 106 |
| 49 | 2.40 | 123 |
| 50 | 2.69 | 100 |
| 51 | 2.46 | 99 |
| 52 | 2.50 | 124 |

*The particle size in the polymer emulsion is determined using dynamic light scattering (DLS) in a dilute aqueous sample of the emulsion at 25° C. ± 1° C.

Example 53

The preparation below is intended to illustrate the present invention without limiting it. Unless stated otherwise, all quantitative data, fractions and percentages are based on the weight and the total amount or on the total weight of the preparation.

The polymer according to the invention is diluted with some of the water phase and added to the surfactant phase with stirring. The other formulation constituents apart from NaOH and the suspended bodies are then added with stirring. After the pH has been adjusted, the suspended bodies are stirred into the finished gel base with as little shear as possible.

TABLE 3

Preparation shower gel

| | |
|---|---|
| Sodium laureth sulfate | 6.50 |
| Cocoamidopropylbetaine | 4.60 |
| Sodium cocoyl glutamate | 0.50 |
| Polymer | 2.25 |
| PEG-40 hydrogenated castor oil | 0.80 |
| PEG-7 glyceryl cocoate | 1.75 |
| Pigments | q.s. |
| NaOH | q.s. |
| Perfume | q.s. |
| Water | ad 100 |

TABLE 4

Results for preparation shower gel

| Example | tan δ | Viscosity in mPas | pH of shower gel |
|---|---|---|---|
| 1 | 0.30 | 3544 | 6.19 |
| 2 | 0.29 | 2600 | 6.21 |
| 3* | 0.89 | 2605 | 6.15 |
| 4* | 8.58 | 1977 | 6.18 |
| 5* | 1.89 | 2014 | 6.15 |
| 6* | 0.59 | 2234 | 6.20 |
| 7* | 1.56 | 1967 | 6.18 |
| 8* | 5.03 | 1548 | 6.19 |
| 9* | 1.54 | 2043 | 6.18 |
| 10* | n.d. | n.d. | n.d. |
| 11* | n.d. | n.d. | n.d. |
| 12* | 8.14 | 1465 | 6.11 |
| 13 | 0.32 | 2404 | 6.18 |
| 14 | 4.54 | 2055 | 6.25 |
| 15 | 0.70 | 1964 | 6.18 |
| 16 | 0.27 | 2423 | 6.15 |
| 17 | 3.57 | 3356 | 6.18 |
| 18 | 0.31 | 2092 | 6.20 |
| 19 | 1.12 | 1998 | 6.18 |
| 20 | 1.92 | 2754 | 6.17 |
| 21 | 4.42 | 2090 | 6.23 |
| 22 | 0.37 | 3118 | 6.23 |
| 23 | 0.35 | 3089 | 6.22 |
| 24 | 0.17 | 3409 | 6.20 |
| 25 | 0.19 | 4100 | 6.22 |
| 26 | 4.42 | 3592 | 5.86 |
| 27 | 0.15 | 2967 | 6.17 |
| 28 | 0.14 | 3301 | 6.15 |
| 29 | 2.58 | 2442 | 6.18 |
| 30 | 2.54 | 1941 | 6.21 |
| 31 | 0.52 | 2233 | 6.15 |
| 32 | 1.83 | 2752 | 6.15 |
| 33 | 0.79 | 2953 | 6.20 |
| 34 | 0.83 | 2208 | 6.21 |
| 35 | 0.24 | 3501 | 6.20 |
| 36 | 0.34 | 2833 | 6.38 |
| 37 | 0.23 | 3432 | 5.91 |
| 38 | 0.20 | 3262 | 6.18 |
| 38 | 0.26 | 3580 | 6.11 |
| 40 | 0.16 | 4120 | 6.25 |
| 41 | 0.39 | 3317 | 6.19 |
| 42 | 0.17 | 3230 | 6.15 |
| 43 | 0.25 | 3690 | 6.15 |
| 44 | 0.22 | 4167 | 6.28 |
| 45 | 5.97 | 3196 | 5.97 |
| 46 | 0.60 | 2385 | 6.14 |
| 47 | 0.26 | 4349 | 6.17 |
| 48 | 0.22 | 4073 | 6.29 |
| 49 | 0.42 | 3313 | 6.09 |
| 50 | 0.37 | 3827 | 5.87 |
| 51 | 0.83 | 3580 | 5.93 |
| 52 | 0.14 | 7344 | 6.07 |

*The examples were prepared without perfume in the shower gel.

The viscosity of the preparations is measured on a rheometer at 25° C.±1° C. with 40 mm cone/plate geometry (1° cone angle) with a gap of 0.03 mm, charging being carried out in a structure-preserving manner. A suitable constant shear rate time ramp is pregiven and a corresponding structure recovery time is observed before the test. The viscosity is given for a shear rate of 10 s$^{-1}$.

Example 54

It has surprisingly been found that the morphology of the polymers produced by a rapid dosing of the monomer mixture is advantageous within the context of the present invention. Table 4 shows the various properties of two polymers when the dosing time is varied. The dosing time is preferably 40 minutes and particularly preferably 30 minutes.

TABLE 5

Dosing time and results

| Polymer | Dosing time | tan δ | Viscosity in mPas |
|---|---|---|---|
| Example 35 | 30 minutes | 0.24 | 3501 |
| Example 35 | 40 minutes | 0.21 | 4114 |
| Example 35 | 50 minutes | 0.49 | 4056 |
| Example 35 | 60 minutes | 1.45 | 3585 |
| Example 24 | 30 minutes | 0.17 | 3409 |
| Example 24 | 50 minutes | 24.26 | 1805 |

Example 55

The polymers according to the invention must have adequate storage stability. For this purpose, a shower gel according to Example 53 was produced again after one year from Examples 1, 22, 24, 25 and 28. It is found that the polymers according to the invention are also advantageous after prolonged storage at room temperature.

TABLE 6

Results of storage stability

| | after 24 h | | after storage | | |
|---|---|---|---|---|---|
| Polymer | tan δ | Viscosity in mPas | Time | tan δ | Viscosity in mPas |
| Example 1 | 0.30 | 3544 | 15 months | 0.24 | 4285 |
| Example 22 | 0.37 | 3118 | 13 months | 0.29 | 4247 |
| Example 24 | 0.17 | 3409 | 13 months | 0.20 | 4083 |
| Example 25 | 0.19 | 4100 | 13 months | 0.22 | 4823 |
| Example 28 | 0.14 | 3301 | 10 months | 0.20 | 3754 |

Example 56

Compared to other polymers, the polymers according to the invention overcome deficiencies in the prior art compared to other polymers.

In order to illustrate this, a shower gel according to Example 53 was prepared in each case from Examples 24, 37 and Carbopol® AQUA SF-1 (Lubrizol).

TABLE 7

Results compared to AQUA SF-1

| | Example 24 | Example 37 | Carbopol® AQUA SF-1 |
|---|---|---|---|
| tan δ | 0.17 | 0.23 | 0.42 |
| Viscosity in mPas | 3409 | 3432 | 3834 |
| Yield point in Pa | 3.6 | 3.4 | 3.3 |
| pH | 6.20 | 5.91 | 6.45 |

TABLE 7-continued

Results compared to AQUA SF-1

| | Example 24 | Example 37 | Carbopol® AQUA SF-1 |
|---|---|---|---|
| Turbidity in NTU | 8 | 9 | 18 (58 at pH 6.20) |

At a lower pH than AQUA SF-1, the polymers according to the invention have a better tan δ and a lower turbidity. Turbidity values of <10 are comparable with spring water. Upon adjusting a preparation containing AQUA SF-1 to a lower pH value, e.g.: 6.20, the preparation is distinctly perceptibly turbid (NTU=58).

What is claimed is:

1. A polymer which is obtained by free-radical emulsion polymerization of monomers comprising
   (A) at least one acidic vinyl monomer or salt thereof,
   (B) at least one nonionic vinyl monomer,
   (C) at least one monomer comprising an unsaturated end group and a polyoxyalkylene portion,
   (D) at least one crosslinking monomer, and
   (E) optionally, a protective colloid, wherein no associative monomers are present,
the polymerization being controlled such that at least at times a gel effect arises, achieved by monomer addition (dosing time) taking place over not more than 40 minutes.

2. The polymer of claim 1, wherein (B) comprises hydrophobic at least one of a $C_{12}$ alkyl acrylate and a $C_{18}$ alkyl acrylate.

3. The polymer of claim 1, wherein the monomer addition takes place over not more than 30 minutes.

4. The polymer of claim 1, wherein (A) comprises one or more monomers selected from vinyl monomers having carboxyl groups and alkali, alkaline earth, ammonium, and alkylammonium salts thereof.

5. The polymer of claim 1, wherein (A) comprises one or more monomers selected from acrylic acid, methacrylic acid, and alkali, alkaline earth, ammonium, and alkylammonium salts thereof.

6. The polymer of claim 1, wherein (B) comprises one or more monomers selected from C1-C22-alkyl (meth)acrylates.

7. The polymer of claim 1, wherein (C) comprises one or more monomers selected from vinylpolyalkylene glycols and polymerizable surfactants.

8. The polymer of claim 7, wherein (C) comprises one or more monomers selected from EO/PO 1,4-butanediol vinyl ether (EO/PO 30 mol), allylpolyalkylene glycol ether (EO 30 mol), allylpolyalkylene glycol ether (EO 20 mol, PO 20 mol), vinylpolyalkylene glycol ether (EO 20 mol), allyl alcohol alkoxylates, polyalkyleneglycol allyl butyl ether (EO 25 mol, PO 8 mol).

9. The polymer of claim 1, wherein (D) comprises one or more monomers selected from polyol (meth)acrylates comprising at least two (meth)acrylate groups, and mixed esters of polyols with at least one of acrylic acid and methacrylic acid.

10. The polymer of claim 1, wherein the polymer comprises from 10% to 75% by weight of (A), from 10% to 90% by weight of (B), from 0.5% to 40% by weight of (C), and up to 1% by weight of (D).

11. The polymer of claim 1, wherein a weight ratio (A):(B) is from 1:2 to 2:1.

12. The polymer of claim 1, wherein (B) comprises ethyl acrylate.

13. A thickened preparation, wherein the preparation comprises one or more polymers according to claim 1.

14. The preparation of claim 13, wherein the preparation comprises from 2% to 3% by weight of the one or more polymers.

15. The preparation of claim 13, wherein the preparation is one or more of a health product, a cleaning product, a household product, a shower gel, a paint, an ink, a dispersant, an antisettling agent, a concrete or cement additive, a coating composition, a medicinal product, a cosmetic product, and a dermatological product.

16. The preparation of claim 13, wherein the preparation has a tan δ of from 0.05 to 0.6.

17. The preparation of claim 13, wherein at a pH of <6.2 the preparation has a turbidity value of NTU <20.

18. A polymer which is obtained by free-radical emulsion polymerization of monomers comprising
  (A) from 35% to 49% by weight of one or more monomers selected from vinyl monomers comprising carboxyl groups and alkali, alkaline earth, ammonium, and alkylammonium salts thereof,
  (B) from 47% to 60% by weight of one or more monomers selected from C1-C22-alkyl (meth)acrylates,
  (C) from 2% to 6% by weight of one or more monomers selected from vinylpolyalkylene glycols and polymerizable surfactants,
  (D) from 0.1% to 0.35% by weight of one or more monomers selected from polyol (meth)acrylates comprising at least two (meth)acrylate groups, and mixed esters of polyols with at least one of acrylic acid and methacrylic acid, and
  (E) optionally, a protective colloid, wherein no associative monomers are present,
the polymerization being controlled such that at least at times a gel effect arises, achieved by monomer addition (dosing time) taking place over not more than 30 minutes.

* * * * *